(12) United States Patent
Gotlib (10) Patent No.: US 10,849,602 B2
(45) Date of Patent: Dec. 1, 2020

(54) METHOD OF CONDUCTING A MINIMALLY INVASIVE SURGICAL PROCEDURE AND RKH-I APPARATUS FOR THE IMPLEMENTATION THEREOF

(71) Applicant: Dmitrii Viktorovich Alenkin, Kaluzhskay obl. (RU)

(72) Inventor: Irina Alekseevna Gotlib, Moscow (RU)

(73) Assignee: Dmitrii Viktorovich Alenkin, Kaluzhskay obl. (RU)

(*) Notice: Subject to any disclaimer, the term of this patent is extended or adjusted under 35 U.S.C. 154(b) by 435 days.

(21) Appl. No.: 15/571,445

(22) PCT Filed: Apr. 19, 2016

(86) PCT No.: PCT/RU2016/000223
§ 371 (c)(1),
(2) Date: Nov. 2, 2017

(87) PCT Pub. No.: WO2016/178599
PCT Pub. Date: Nov. 10, 2016

(65) Prior Publication Data
US 2018/0132833 A1 May 17, 2018

(30) Foreign Application Priority Data
May 6, 2015 (RU) .................................. 2015117193

(51) Int. Cl.
*A61B 34/30* (2016.01)
*A61B 10/02* (2006.01)
(Continued)

(52) U.S. Cl.
CPC ............ *A61B 10/04* (2013.01); *A61B 5/1135* (2013.01); *A61B 6/032* (2013.01); *A61B 6/12* (2013.01);
(Continued)

(58) Field of Classification Search
CPC ...... A61B 10/0233; A61B 6/032; A61B 34/30
See application file for complete search history.

(56) References Cited

U.S. PATENT DOCUMENTS 5,894,841 A * 4/1999 Voges .................. A24F 47/008
128/203.12
2003/0097060 A1 5/2003 Yanof
(Continued)

FOREIGN PATENT DOCUMENTS

KG         1499 C1    11/2012
RU    2001128777 A    11/2003
(Continued)

*Primary Examiner* — Jason M Ip
(74) *Attorney, Agent, or Firm* — Craft Chu PLLC; Andrew W. Chu (57) ABSTRACT

An automatic robotic apparatus for conducting a minimally invasive surgical procedure includes a robotic arm having a movable member made as the multilink active actuator. The end portion of the multilink active actuator is provided with the connector to which the hollow head for a needle biopsy is attached. The operation of the U-shaped head is under full control of the robotic apparatus computer system. Results of pre-procedure studies of a site of interest and the progression of the surgical procedure are displayed on a monitor of the computer system.

19 Claims, 3 Drawing Sheets

(51) Int. Cl.
    *A61B 34/32*   (2016.01)
    *A61B 6/03*    (2006.01)
    *A61B 17/00*   (2006.01)
    *A61M 19/00*   (2006.01)
    *A61B 6/00*    (2006.01)
    *A61B 34/10*   (2016.01)
    *A61B 90/50*   (2016.01)
    *A61B 5/055*   (2006.01)
    *A61B 10/04*   (2006.01)
    *A61B 5/113*   (2006.01)
    *A61B 34/00*   (2016.01)
    *A61B 6/12*    (2006.01)
    *A61M 5/32*    (2006.01)
    *A61B 6/04*    (2006.01)
    *A61M 5/00*    (2006.01)

(52) U.S. Cl.
    CPC .... *A61B 10/0233* (2013.01); *A61B 17/00234* (2013.01); *A61B 34/25* (2016.02); *A61B 34/30* (2016.02); *A61B 34/32* (2016.02); *A61B 34/76* (2016.02); *A61M 5/3298* (2013.01); *A61M 19/00* (2013.01); *A61B 5/055* (2013.01); *A61B 6/0407* (2013.01); *A61B 6/481* (2013.01); *A61B 6/485* (2013.01); *A61B 6/541* (2013.01); *A61B 6/582* (2013.01); *A61B 2010/045* (2013.01); *A61B 2034/107* (2016.02); *A61B 2034/302* (2016.02); *A61B 2034/306* (2016.02); *A61B 2090/502* (2016.02); *A61M 2005/006* (2013.01)

(56) References Cited

U.S. PATENT DOCUMENTS

| 2004/0111183 | A1* | 6/2004  | Sutherland | A61B 34/77  |
|              |     |         |            | 700/245     |
| 2004/0254773 | A1* | 12/2004 | Zhang      | A61B 6/541  |
|              |     |         |            | 703/11      |
| 2009/0082784 | A1* | 3/2009  | Meissner   | A61B 34/30  |
|              |     |         |            | 606/130     |
| 2009/0112119 | A1  | 4/2009  | Stanley    |             |
| 2009/0253998 | A1* | 10/2009 | Chen       | A61B 17/0482|
|              |     |         |            | 600/565     |
| 2010/0274202 | A1* | 10/2010 | Hyde       | A61B 5/150106|
|              |     |         |            | 604/272     |
| 2012/0245560 | A1* | 9/2012  | Hochman    | A61M 5/1452 |
|              |     |         |            | 604/518     |

FOREIGN PATENT DOCUMENTS

RU    2362490 C1    7/2009
RU    2382593 C1    2/2010

* cited by examiner

METHOD OF CONDUCTING A MINIMALLY INVASIVE SURGICAL PROCEDURE AND RKH-I APPARATUS FOR THE IMPLEMENTATION THEREOF

CROSS-REFERENCE TO RELATED APPLICATIONS

See Application Data Sheet.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

Not applicable.

BACKGROUND OF THE INVENTION

1. Field of the Invention

The proposed group of inventions relates to the field of medicine, to minimally invasive method of surgical procedure, in particular to a needle biopsy of organs of the chest, the abdominal cavity, the small pelvis and the limbs, as well as to corresponding medical equipment for carrying out a needle biopsy.

2. Description of Related Art Including Information Disclosed Under 37 CFR 1.97 and 37 CFR 1.98

Several decades ago, a malignant nature of encapsulated tumors was established by using a complex and risky method (see, Volkov P. T. "Clinical picture, diagnostics and surgical treatment of neoplasms in the mediastinum" (in Russian), L., 1970 [1]). The method taught in the source [1] comprises operative dissection of the chest and collection of a tissue piece. As a rule, a transpleural and intercostal incision was made. Furthermore, other operative methods (also, see [1]) included median sternotomy, upper mediastinotomy through a neck incision, anterolateral, posterolateral or lateral thoracotomy. Naturally, an operative access for collection of a biopsy piece was selected after a X-ray determination of a neoplasm.

Upon a time, a needle biopsy was used for determining a tumor nature.

A needle biopsy is known as a minimally invasive procedure lacking disadvantages of a surgical biopsy [1], including the necessity of making extensive incisions of the skin and giving general anesthesia. A needle biopsy is a reliable method for collecting tissue samples, which enables to confirm a benign or malignant nature of a neoplasm. This procedure is not accompanied by a severe pain and is comparable, as to its result accuracy, to surgical biopsy [1]; recovery after a needle biopsy goes rather quickly, and patients may return to their normal life soon.

A method for collecting a mediastinal biopsy material is known in the art (see, RU 94009373, A61B 17/34, publ. 1996 [2]).

This method for collecting a biopsy material comprises an X-ray determination of a neoplasm location and a biopsy, and a biopsy tissue is collected through the breastbone, a biopsy tissue being collected with the use of a needle intended for biopsy of the parenchymal organs.

It is obvious that the known method [2] lacks disadvantages of surgical biopsy [1] in the process of which, in particular due to extended skin incisions made under narcosis, a bleeding may occur that results from a damage of vessels, organs adjacent to the tumor, suppuration and other damages.

However, according to the known solution [2], a sternotomic biopsy is carried out without anesthesia, using a needle for puncturing the parenchymal organs, a required introduction depth being marked on the needle beforehand. Obviously, this approach is extremely dangerous for the patient health, since the breastbone is punctured without any surface and intracutaneous anesthesia. Thus, in fact, a surgeon punctures the breastbone intuitively, being oriented only by a supposed location of a tumor; so, a probability of error and damage of organs adjacent to a tumor really exists. Moreover, without preliminary anesthesia a patient's reaction to a needle entering the chest may be unpredictable, a pain shock is possible that may cause a loss of consciousness and a body shift during entering of a needle, and, as a result, a damage may be caused to patient internal organs, or other consequences severely affecting the patient's health may occur.

A method of conducting a transcutaneous needle biopsy (see, RU 2362490, A61B 10/02, publ. 2009 [3]) is the closest analog of the proposed method of conducting a minimally invasive surgical procedure.

The known method of conducting a transcutaneous biopsy [3] comprises a preliminary evaluation of a site, dimension, and structure of a focal lesion, selection of a point optimal for puncturing with the use of computed tomography (CT), and a needle biopsy of the focal lesion with the use of a biopsy needle having a length of not more than 20 cm.

The essence of the known method of conducting a transcutaneous biopsy [3] is that a standard pre-medication is carried out, and a CT study is conducted wherein a site, dimension, structure, areas of interest, etc. are evaluated. Then, the skin is punctured with a scalpel manually in the selected point, and then 2-3 needles are advanced to a depth of 2-4 cm (up to muscles) through a puncture made in the skin, and CT is conducted. A needle having the optimal direction is determined on the CT scan display, and a distance from the needle end to the border of the focal lesion is measured. The selected needle is moved toward the border of the focal lesion, and the other needles are removed. After leading the needle to the focal lesion border (site of interest), the patient is removed from the CT scan aperture, and the mandarin is removed from the needle. A biopsy needle with a biopsy gun, which is preliminarily attached and cocked, is advanced to the depth equal to the mandrin length, and, fixing the gun, a biopsy of the focal lesion is conducted.

This methodology of conducting a needle biopsy [3] is rather comfortable and painless for a patient owing to pre-operation arrangements and pre-medication including anesthesia. A tissue sample, as obtained according to this methodology [3] and capable of being assessed visually, is sent to a laboratory for a histological study.

However, the known technology of conducting a needle biopsy [3] is not free from some disadvantages. Surely, a CT scan of a focal lesion enables to select an optimal point for puncturing and a correct trajectory for leading a needle, but, actually, the whole main procedure is conducted manually with the use of 20 cm needles used simultaneously, and their clumsy use may cause a serious damage to a patient; moreover, a patient is periodically removed from the CT scan aperture for a short time, which may result in his/her excess anxiety and doubt in operation success, and the appearance of 20 cm needles may aggravate the situation greatly. Thus, success of the whole operation according to the known technology [3] depends mainly on a surgeon conducting it, and the patient's health and life will depend on his/her experience, talent and qualification level.

The above-described variants of surgical procedures are conducted solely manually, under the full control of experienced surgeons, but the number of talented and experienced surgeons in the world, who may provide high guarantees for conducting reliable and successful operations, is limited; and this, in turn, provides a stimulus to those skilled in the art for developing automated systems with minimum human involvement for conducting various surgical procedures and interventions reliably and successfully.

The robotized surgery started developing in 1980s. One of the first automated surgical apparatus was the da Vinci robot. Its first variant was developed in the end of 1980s; and by 2010 more than 1,000 "da Vinci" robots have been constructed that are successfully used in hundreds of medical institutions worldwide.

The da Vinci robotic surgical system is a commercial product of Intuitive Surgical Co. The robot consists of two units, one for an operator, and the second performs the functions of a surgeon. The surgeon sits at the console, which provides the possibility of 3D viewing a site of the procedure at multiple magnification, and manipulates special joysticks for controlling the tools. The da Vinci robot conducts various procedures, such as mitral valve repair, cardiac tissue ablation, gastric bypass, lung lobectomy, mediastinal tumor resection, ureteral reimplantation, thyreoidectomy, etc. etc. (see, e.g., https://en.wikipedia.org/wiki/Da_Vinci_Surgical_System [4]).

However, the da Vinci robot is not designed for conducting minimally invasive surgical procedures, such as a needle biopsy.

An automated apparatus for biopsy of the parenchymal organs with simultaneous spectroscopic inspection is known in the art (see, RU 2529629, A61B 10/02, publ. 2014 [5]).

This automated apparatus for biopsy with simultaneous spectroscopic inspection [5] comprises a radiation source, a fiber for radiation delivery connected thereto, a registration unit, a computer with software, an biopsy attachment that collects and holds a tissue sample.

The essence of the procedure of parenchymal organ biopsy with the use of the apparatus for biopsy with simultaneous spectroscopic inspection (see, [5]) consists in that laser radiation from a source enters a light guide and from there to a biopsy tube. Radiation exiting from the fiber within the tube interacts with a biologic tissue. Scattered laser radiation enters, together with fluorescent radiation, into receiving fibers, then into a spectrometer, and after that radiation is formed into a spectrum and projected onto a linear photodiode array. The registration unit transmits digitized information to a computer which processes the information received. In order to collect a tissue sample, air within the biopsy tube is drawn into a syringe, and, as the result, the tissue sample enters the biopsy tube. In order to extract the tissue sample from the biopsy tube into a vial, it is necessary to pass air or liquid therethrough with the use of a syringe.

The known apparatus for biopsy (see, [5]) is automated only partially, and a surgeon has to participate in the apparatus operation practically in all stages; in particular, a surgeon has to collect and wash out a tissue sample to be studied with the aid of a syringe; so, reliability and success of a biopsy procedure fully depends on professionalism and talent of a surgeon. Furthermore, the whole biopsy procedure conducted with the aid of the known apparatus for biopsy [5] requires too much time for a plurality of preparation steps consisting in oral introduction of a 5-aminolevulinic acid hydrochloride solution into the patient's organism (several hours before the beginning of the biopsy main procedure) and in the apparatus setting-up comprising the following stages: turning the laser on, spectrometer calibration, computer setup, ultrasonic scan apparatus setup according to controls for required conduction of a biopsy procedure, spectroscopic data analysis and calculation of tumor markers concentrations. Thus, the above-said disadvantages of the known apparatus for biopsy [5] are obvious and may negatively affect results of a biopsy procedure conducted with the aid of the known apparatus for biopsy [5].

A system for conducting a biopsy procedure is known in the art (see, RU 2510699, A61B 10/02, publ. 2012 [6]).

This system for biopsy [6] comprises a visualization system for obtaining diagnostic images of a target site, a device comprising an extending needle for conducting a biopsy procedure, a tracking system for a biopsy needle, a visualization system for obtaining images of a target site, and a computer system coupled with the tracking system and the visualization system.

The known system for biopsy [6], similarly to the apparatus for biopsy [5], is not fully automated and needs periodical interventions of an experienced surgeon performing setup and adjustment of the system operation; in particular, a surgeon is allowed to manually align a probe and the visualization system. Hence, it would be obvious for those skilled in the art that, nevertheless, success of a procedure being conducted with the aid of the system for biopsy [6] depends mainly on the human factor, namely, on professionalism, talent and expertise of a surgeon monitoring the course of this procedure and making required and most important corrections in it.

The closest analog for the proposed apparatus for minimally invasive surgical procedure is a robotic system intended for conducting minimally invasive surgical procedures (see, U.S. Pat. No. 6,785,572, A61B 10/02, publ. 2004 [7]).

This robotic system [7] comprises an imaging apparatus for obtaining diagnostic images of a target site, which, intermittently during the procedure, obtains, upon demand, real-time medical images of the actual procedure that are displayed on a computer monitor, a robotic arm with a gripper having an end-effector in which a biopsy needle is held, movement of said needle being monitored by a computer system and displayed on its monitor.

This robotic system is fully automated and does not require any manual interventions or corrections by a surgeon during operation. When in operation, a detector measures the parameters of a biopsy needle, in particular a needle pressure force, a needle position, and an inclination angle, which are transmitted to a computer system processing the received signals with the aid of special software and transmitting data required for automatic correction of biopsy needle parameters to a haptic control system. A virtual planning view is displayed on the monitor screen of the computer system, which ensures reliability of a medical procedure with biopsy needle preferred parameters required for its successful conduction. However, a biopsy procedure conducted with the aid of this robotic system [7] is associated with a high probability of the sense of strong anxiety and danger for life arising in a patient, since a biopsy needle of a great length is used in the procedure, the patient lies on his/her back and is fully conscious, and, moreover, the biopsy needle is not covered, and the patient finds himself/herself in a rather narrow space aggravating his/her uneasy condition formed shortly before a needle biopsy.

In this connection, for the purposes of comfortable and safe conduction of the procedure in a patient, there exists a need of using biopsy needles, which are precluded from coming into the patient's field of view of a patient, in automated surgical apparatuses for minimally invasive surgical procedures. An apparatus for biopsy is known in the art (see, RU 2177751, A61B 17/34, publ. 2002 [8]).

A biopsy needle in this apparatus for biopsy [8] is placed into a cylindrical case. An important feature of the apparatus operation is that the lower end of the case is submerged into liquid nitrogen for 5 seconds. After that, the cooled apparatus is arranged onto a site of interest with its working end. Then, a needle is put into the case, its tip is brought into a contact with a frozen tissue, and a tissue sample is collected by translational and rotational motion of the needle.

Because a biopsy needle in this apparatus [8] is placed into a cylindrical case, a patient cannot see it during the procedure, but this apparatus is similar in its shape to a medical syringe, and in this connection an uneasy feeling arises in patients with strong nervous irritability, which may cause a pernicious effect during a needle biopsy with the use of this apparatus. Furthermore, this apparatus [8] is designed solely for use in the manual mode by a professional surgeon, and reliability and success of such a procedure depends on his/her professionalism; moreover, a possibility of using this apparatus in a robotic system for conducting minimally invasive surgical procedures is not provided for.

A tissue puncture device is known in the art (see, U.S. Pat. No. 8,197,504, A61B 17/34, publ. 2012 [9]).

A biopsy needle in this device [9] is placed into a suction device in the form of a cup which open end contacts a tissue site of interest.

A distinctive feature of this device [9] is that vacuum is created within the cup, which ensures drawing the tissue site of interest into the cup for effecting a puncture and subsequent collection of a tissue sample.

This device [9] is comfortable, reliable and safe in use; it may be adapted for operation in the automatic mode in robotic apparatuses designed for conducting minimally invasive surgical procedures, but this device [9] has a very narrow field of application—it is used solely for advancing a biopsy needle into gastric wall tissues for the purpose of collecting a tissue sample.

The closest analog of the proposed apparatus for conducting minimally invasive surgical procedures is a needle biopsy device used in a robotic system for conducting minimally invasive surgical procedures (see, US2009112119, A61B 10/02, publ. 2009 [10]).

This device [10] is made in the form of a cannula which working end is provided with a collar, and a biopsy needle with mechanisms that drive it into the operating condition.

This biopsy device [10] is successfully used in a robotic system for conducting surgical procedures, has a wide field of application, is comfortable and easy in operation, does not provoke uneasy conditions in children, persons of advanced age and persons with nervous hyperirritability. A minimally invasive surgical procedure conducted with the aid of the device [10] goes on mainly in the automatic mode, so success and reliability of the procedure does not depend on professionalism and talent of a surgeon under whose control a needle biopsy is conducted.

Speaking about disadvantages of this device [10], one may mention its complex structure enabling to impart rotational and translational motion to a biopsy needle, and a complex configuration and shape of a biopsy needle itself, which, in turn, results in complications in the production process and, correspondingly, to an increase in the market cost of the device and the robotic system designed for conducting surgical procedures. Apart from this, in a needle biopsy procedure the cannula may partially move out of its place of initial fixation due to the fact that said cannula is fixed on the patient's body with the aid of a strap covering the body from two sides. Thus, the idea of fixing a cannula on the patient's body for conducting a needle biopsy is developed with insufficient reliability in the device [10].

BRIEF SUMMARY OF THE INVENTION

The objective of the proposed group of inventions united by the single inventive concept is to create a single innovative fully automated method of conducting a needle biopsy procedure, the method exhibiting high medical parameters and performance, enabling patients to spend less time for post-procedure recovery, and, moreover, not requiring continuous human monitoring over the method functioning and intervention of a servicing personnel in the course of a needle biopsy procedure.

The technical effect of the proposed automated robotic apparatus for conducting a minimally invasive surgical procedure is higher reliability when collecting tissue samples enabling to confirm a benign or malignant nature of a neoplasm, higher accuracy when conducting direct surgical procedure, reduced possibility of damaging critical organs and, as a consequence, a significantly reduced possibility of developing complications.

This technical effect is achieved due to the fact that the automatic robotic apparatus for conducting a minimally invasive surgical procedure comprises a robotic arm which movable member comprises, at its end section, a means for conducting a transcutaneous needle biopsy which operation is monitored by a computer system and the operation course is displayed on its monitor, said robotic arm comprising a pressurized anesthetic and a pressurized antiseptic, a means used for giving deep anesthesia, and a control unit cooperating with servo drives made capable of being controlled mechanically, said movable member and a means for conducting a transcutaneous needle biopsy that is made in the form of a U-shaped head accommodating an output through hole for supply of an anesthetic and an antiseptic for surface anesthesia, a guide intratissular anesthesia needle, a guide needle for needle biopsy and a mechanism unit for controlling said needles; the computer system is made capable of receiving and processing CT virtual slices of a focal lesion that are transmitted by the CT scanner and capable of mapping out the course and subsequently modeling a minimally invasive surgical procedure with the aid of a special software.

According to a preferable embodiment of the automatic robotic apparatus, the antiseptic and the anesthetic are contained in aerosol cylinders.

According to another preferable embodiment of the automatic robotic apparatus, the robotic arm is made capable of being fixedly attached to the floor or to the ceiling.

According to a specific embodiment of the automatic robotic apparatus, the robotic arm is capable of moving, since it is equipped with movable wheels.

The robotic arm may be provided with an emergency stop means triggered by pushing an instant shutoff button.

A means used for giving deep anesthesia is reasonably made as a piston mechanism provided with an electric motor.

Preferably, the piston mechanism is put in a cylindrical container.

According to a preferable embodiment of the automatic robotic apparatus, the movable member of the robotic arm is made as an active multilink actuator.

The proposed automatic robotic apparatus may conduct a reliable minimally invasive surgical procedure, namely a needle biopsy procedure; and this apparatus does not make extended incisions of the skin and does not use general anesthesia for conducting said procedure. This apparatus enables to conduct a reliable and fast collection of tissue samples enabling to confirm a benign or malignant nature of a neoplasm.

Owing to the fact that the robotic arm contains a pressurized anesthetic and a pressurized antiseptic as well as the means for conducting intratissular anesthesia, it becomes possible to instantly disinfect the patient's skin surface and release an anesthetic for surface anesthesia from the output through hole located within the U-shaped head for effecting a puncture, after which the guide intratissular anesthesia needle is immediately advanced through the patient's skin and under the skin layer-by-layer, thus introducing an anesthetic in accordance with the conditions formed with the aid of a special software and preset in the automatic mode earlier.

Owing to the fact that the movable member of the robotic arm, which accommodates a biopsy needle and the control mechanism unit, is made as an active multifunctional multilink actuator, and the servo drives are coupled with the control unit receiving parameters and conditions of a surgical procedure and are made capable of controlling the actuator and, consequently, the U-shaped head, and owing to the fact that the computer system is made capable of receiving and processing CT virtual slices of a focal mass, which are transmitted by the computer system of a CT scanner; and owing to the fact that the computer system is made capable of mapping out a course and subsequently modeling a procedure to ensure an error-free robotic minimally invasive surgical procedure the reliability of tissue sample collection is increased, since the computer system selects conditions and parameters so as to cause minimal harm to neighboring organs; the accuracy of a direct surgical procedure is increased, since optimal parameters and conditions for advancing a biopsy needle are selected in a computerized analysis, enabling to direct said needle to a required site with extreme accuracy and reducing the possibility of damaging critical organs; and, taking into account the above facts, the risk of developing possible complications is reduced.

The technical effect of the proposed method of conducting a minimally invasive surgical procedure is a shorter time required for it, increased reliability of collecting tissue samples enabling to confirm a benign or malignant nature of a tumor, minimized painful sensations during a surgical procedure, a reduced possibility of damaging critical organs and, consequently, a significantly reduced possibility of developing complications, a shorter time required for the patient's recovery after a needle biopsy procedure, and a precluded influence of ionizing radiation on the service personnel of the robotic apparatus.

The stated technical effect is achieved by that the method of conducting a minimally invasive surgical procedure comprises the evaluation of localization and parameters of a focal mass as well as the selection of a puncture site with the aid of a CT scanner and the conduction of a transcutaneous needle biopsy of a focal mass with the aid of a biopsy needle; CT virtual slices, as produced by the CT scanner computer system, are sent to the computer system of the automatic robotic apparatus, which conducts a minimally invasive surgical procedure, maps out the course of and models a needle biopsy, and said 3D CT virtual slices of a focal mass, as received by the computer system, are subjected to a computerized analysis for the purpose of automatically setting up optimal parameters and conditions for a robotic surgical procedure performed by the U-shaped head of the robotic arm movable member, a biopsy needle and the mechanism unit for controlling it mechanically being located within the head; upon determination of said parameters and conditions, the U-shaped head contacts a patient's skin site, surface and intratissular anesthesia of said site is given, and the biopsy needle is advanced further through the skin for collecting a sample; all this is performed in accordance with preset parameters and conditions for a corresponding surgical procedure during which a CT scanner scans and projects the course of the procedure onto a computer system monitor.

Most preferably, 3D CT virtual slices of a focal mass are subjected to a computerized analysis for the purpose of automatically locating a virtual contact point of the U-shaped head and the patient's body surface by planning and modeling safe movement of the active multilink actuator to the contact point; points of entry and routes of the guide intratissular anesthesia needle, steps of surface and intratissular anesthesia as well as a site and routes for a biopsy needle for collecting a tissue sample are all determined.

It would be reasonable to determine said points of entry of the guide intratissular anesthesia needle and the biopsy needle by finding the air-skin interface according to a HU density (on the Hounsfield scale).

According to a preferred embodiment, routs of the intratissular anesthesia needle are determined by a difference between a density of the skin and that of the muscular tissue layers.

Most preferably, routs for the needles are determined with the possibility of correcting the procedure course by the operator.

Most preferably, routs for the biopsy needle are determined with due regard to the possibility of minimally acting on vessels and critical organs of a patient.

According to a specific embodiment of the proposed method, a minimal action on vessels and critical organs of a patient is ensured by conducting CT scanning with intravenous contrasting or by conducting a MRI scanning procedure.

It would be reasonable to connect a means for monitoring respiratory excursion to the robotic arm for monitoring the patient's breathing; for this, a strap is attached to the patient, which monitors changes in the chest volume. According to a specific embodiment of the method, medical glasses are put onto the patient's eyes, which display data on his/her respiration during scanning and data received in real time.

It would be reasonable, if the patient makes an inhalation that is equal in depth to an inhalation during scanning.

According to a specific embodiment of the method, before determining parameters and conditions for conducting a surgical procedure the robotic arm is calibrated according to the CT scanner coordinates. Preferably, calibration is made with the aid of a U-shaped head for puncture, which is moved by the active multilink actuator of the robotic arm until its marks are superposed with the marks of the CT scanner lasers, and then the robotic arm is fixed in place with retainers.

The proposed method is most appropriately used for conducting a minimally invasive surgical procedure, namely, a needle biopsy of the chest organs, the small pelvis, the abdominal cavity and the limbs.

The proposed robotic automatic method of conducting a needle biopsy procedure does not exhibit disadvantages of the known method of surgical biopsy procedure, including the necessity of making extended skin incisions and giving general anesthesia.

According to the proposed robotic method, CT virtual slices of a focal mass, as produced by the CT scanner computer system, are sent to the computer system of the automatic robotic apparatus conducting a minimally invasive surgical procedure, the computer system of the proposed automatic apparatus mapping out the course and modeling a needle biopsy procedure, and said virtual 3D CT slices of a focal mass, as received by it, are subjected to a computerized analysis for the purpose of determining optimal parameters and conditions with the aid of a special software for conducting a corresponding robotic surgical procedure.

This technique ensures improved reliability of collection of tissue samples enabling to confirm a benign or malignant nature of a tumor, since the computer system selects conditions and parameters that cause minimum harm to neighboring organs; the possibility of damaging critical organs is reduced, since during a computerized analysis optimal parameters of advancing a biopsy needle are selected that enable to advance the needle to a definite site with extreme accuracy, which, in turn, reduces the possibility of developing possible complications and, consequently, reduces time required for post-procedure recovery of a patient.

Owing to the fact that all conditions and parameters of a needle biopsy procedure are known directly before it, the procedure quality is improved significantly and a time period of conducting it is shortened, since such a procedure is conducted in the robotic error-free mode according to a pre-formed program, without spending time for studying internal organs directly during the biopsy collection procedure in order to conduct it in an excellent and reliable way.

Due to surface and intratissular anesthesia of a site selected in a patient and subsequent transcutaneous advance of a biopsy needle for collecting a sample, painful sensations are minimized, and maximum comfort during the whole surgical procedure is ensured for a patient.

Moreover, in essence, the whole minimally invasive automatic robotic surgical procedure, as proposed herein, is conducted on a table within the CT scanner gantry, so any action of X-ray radiation on the service personnel is practically fully excluded.

The technical effect of the proposed apparatus for conducting a transcutaneous needle biopsy procedure is minimization of a skin integrity damage, significant reduction of the risk of developing an infection and complications, such as bleeding, pneumothorax and atelectasis of the lungs, improved reliability and accuracy of the procedure, improved fixation on a patient's skin site of interest, minimization of painful sensations as well as a reduced possibility of damaging critical organs.

Figure 2:
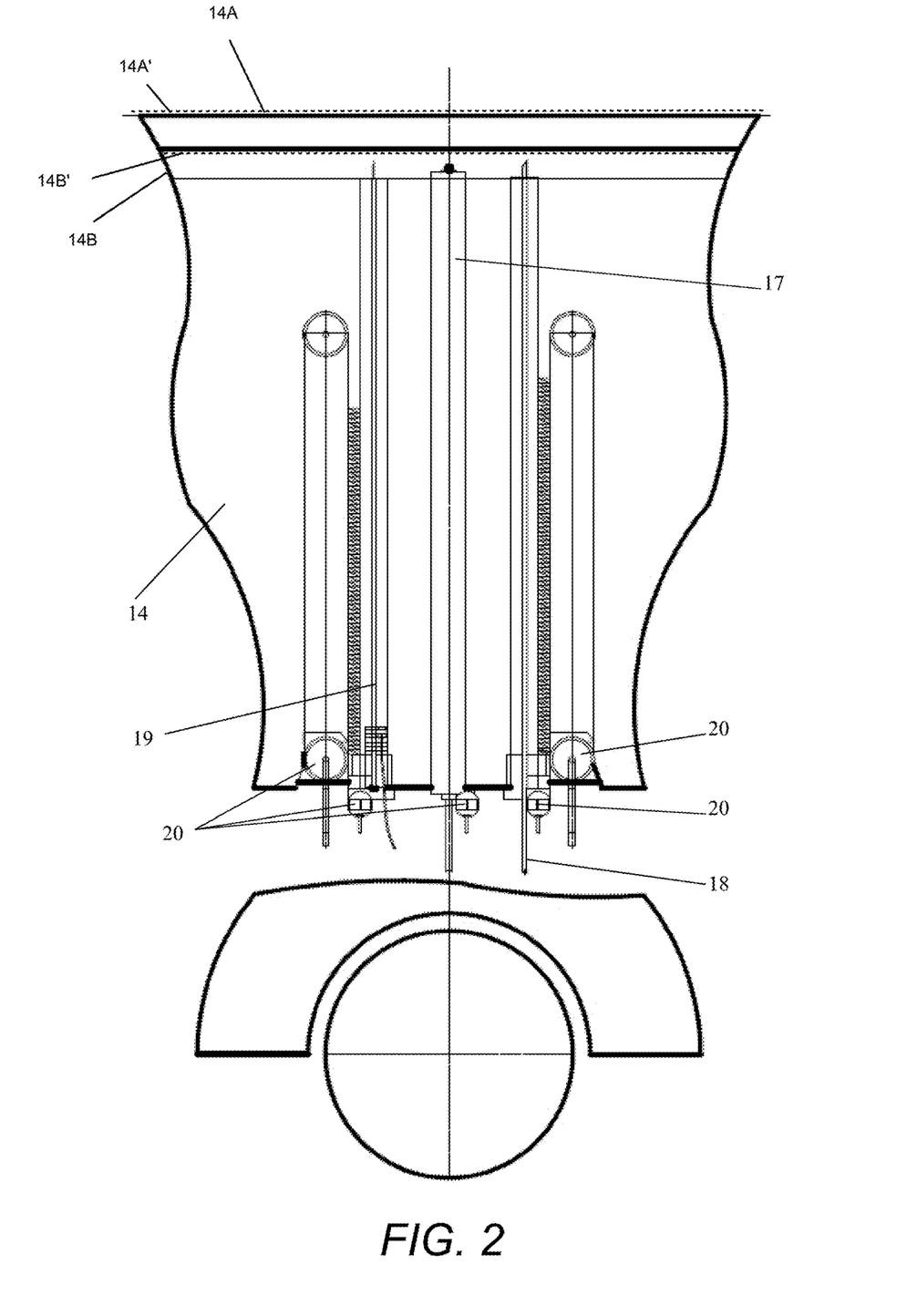
FIG. 2 shows a longitudinal sectional view of the proposed head for conducting a surgical procedure, such as a needle biopsy.

The stated technical effect is achieved by an apparatus for conducting a transcutaneous needle biopsy, comprising: a biopsy needle arranged within a hollow head 14 of U-shaped longitudinal section with an open base end 14A with an open base width 14A' to be fixed on a patient's skin site, the head being made with a width variable along its height, the a base width portion 14B with a base width 14B' being increased toward said patient's skin site, and an output through hole being located within the head, serving for delivering an anesthetic and an antiseptic for surface anesthesia; a guide intratissular anesthesia needle; and a unit accommodating mechanisms controlling delivery of said surface anesthesia and all the needles in accordance with optimal parameters and conditions of a robotic needle biopsy procedure, as automatically preset beforehand. [72] The proposed head of U-shaped longitudinal section is made with a width variable along its height, the base width portion 14B with a base width being increased toward a selected patient's skin site. This constructive approach, due to suction properties of this construction with a variable width and a kind of an annular shoulder, ensures most appropriate engagement of the head and the patient's skin with its slight suction into the head. The proposed head construction, per se, ensures significant reduction of a possibility of developing an infection, since a skin site affected is, in essence, covered by the head, which precludes any infection from entering through holes made by the needles.

According to the proposed invention, the head accommodates: a biopsy needle, a hole for delivering an anesthetic and an antiseptic for surface anesthesia, a intratissular anesthesia needle, and a control unit for controlling the course of anesthesia and all the needles. This enables to reduce a possible damage of the skin, and, consequently, painful sensations to a minimum (only thin needles are used). The control unit for the proposed head is made capable of receiving and processing information from the computer system of the robotic apparatus for the purpose of controlling the needles and anesthesia in full compliance with preset optimal parameters and conditions of conducting a robotic transcutaneous needle biopsy, which, in turn, enables to improve reliability and accuracy of the procedure, while ensuring a significant reduction in the possibility of damaging critical organs.

DETAILED DESCRIPTION OF THE INVENTION

Below, the proposed group of inventions is explained by a specific embodiment which, nevertheless, is not a single possible one, but is used for clear demonstration of a way how the totalities of essential features may achieve the objectively arising technical effect that solves the technical task as set for the group of inventions.

Figure 1:
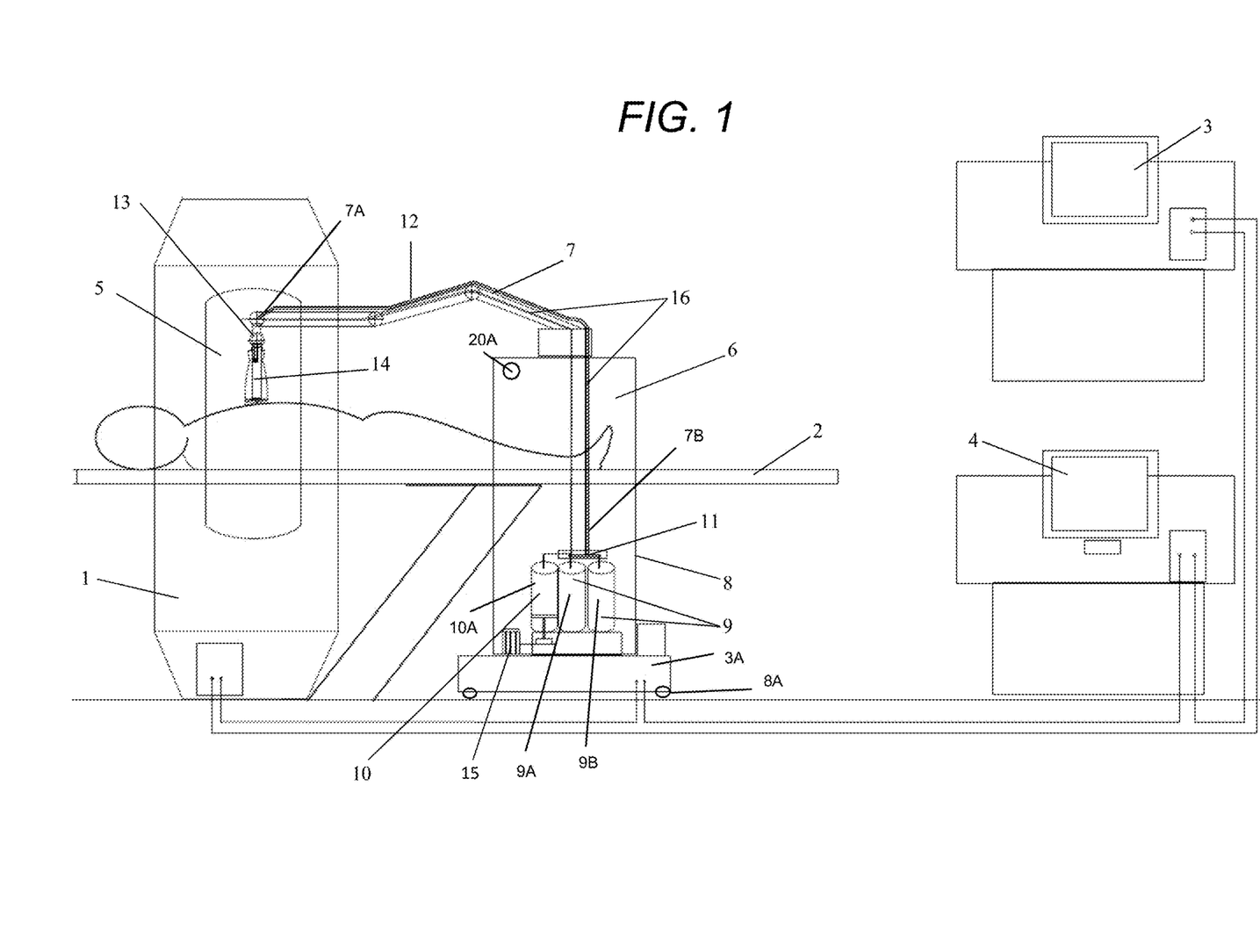
FIG. 1 shows a general schematic view of the proposed automatic robotic apparatus connected to a CT scanner with its own computer system.

The proposed automatic robotic method of conducting a minimally invasive surgical procedure utilizes the following devices and members:
- a CT scanner 1;
- a CT scanner table 2;
- a CT scanner computer system 3;
- a control unit 3A;
- a robotic apparatus computer system 4;
- a CT scanner gantry aperture 5;
- a robotic arm 6;
- an active multilink actuator or movable member 7 having a distal end portion 7A and a proximal end portion 7B;
- a robotic arm case 8 with wheels 8A;
- aerosol cylinders (a pressurized anesthetic cylinder and a pressurized antiseptic cylinder) for an anesthetic 9A and an antiseptic 9B;
- a piston mechanism 10 for surface anesthesia within a cylindrical container 10A;
- rubber tubes 11;
- active actuator links 12;
- a connector 13;
- a hollow head 14 for a needle biopsy;
- a piston mechanism electric motor 15;
- servo drives 16;
- a through hole 17 for delivery of surface anesthesia drugs;
- a guide intratissular anesthesia needle or anesthetic guide needle 18;
- a puncture or biopsy guide needle 19 for a needle biopsy;
- a mechanism control unit or needle control unit 20 controlling said needles and delivery of surface anesthesia drugs;
- an instant stop button 20A.

An automatic robotic apparatus for conducting a minimally invasive surgical procedure comprises the robotic arm 6 which movable member is made as the multilink active actuator 7. The end portion of the multilink active actuator 7 is provided with the connector 13 to which the hollow head 14 for a needle biopsy is attached.

The operation of the U-shaped head 14 is under full control of the robotic apparatus computer system 4. Results of pre-procedure studies of a site of interest and the progression of the surgical procedure are displayed on a monitor of the computer system 4.

The robotic arm 6 comprises the aerosol cylinders 9 with a pressurized anesthetic and a pressurized antiseptic, a means for storage and delivery of deep anesthesia drugs that is made as the piston mechanism 10 provided with the electric motor 15 and a control unit.

This control unit cooperates with the servo drives 16 capable of mechanically controlling the active multilink actuator 7 and the hollow U-shaped head 14 directly used for conducting a minimally invasive surgical procedure, namely, a needle biopsy procedure.

The hollow U-shaped head 14 accommodates the output through hole 17 intended for delivery of an anesthetic and an antiseptic for surface anesthesia, the guide intratissular anesthesia needle 18, a guide needle 19 for a needle biopsy, and a control mechanism unit for the needles and delivery of the surface anesthesia drugs.

The robotic apparatus computer system 4 is made capable of receiving and processing virtual CT slices of a focal mass that are transmitted by the CT scanner computer system 3 and capable of mapping out the course and subsequently modeling a minimally invasive surgical procedure with the aid of a special software.

The robotic arm 6 is equipped with an emergency stop means triggered by pushing an instant stop button.

The proposed group of inventions may be implemented as follows. The proposed automatic robotic apparatus consists, in essence, of the movable robotic arm 6 being controlled by the computer system 4.

Before starting a procedure with the movable automatic robotic apparatus, it should be calibrated in accordance with the coordinates of the CT scanner 1. However, when the apparatus is stably fixed, no calibration before each minimally invasive surgical procedure is required.

After calibration of the proposed automatic robotic apparatus, the CT scanner isocenter is taken as the zero point (x0; y0; z0). Movements are effected along the Y and X axes due to movements of the active multilink actuator 7. The limitations are the size of the gantry aperture of the CT scanner 1 and the size of the U-shaped head 14 arranged at the end of the active multilink actuator 7. Movements along the Z axis are effected due to movements of the CT scanner table 2. After calibration, the coordinate x0y0z0 corresponds to the tip of the biopsy needle 19. After receiving data on a patient, the robotic apparatus computer system 4 receives images in the DICOM format from the CT scanner computer system 3. The patient's body edges are determined by a difference in an air-tissue density in the HU units. Also, possible coordinates are determined for safe manipulative movements of the active multilink actuator 7 and the U-shaped head 14 of the robotic arm 6 in the CT scanner aperture.

In order to conduct a calibration procedure when the automatic robotic apparatus is movable, the operator arranges it near the CT scanner 1 and moves the active multilink actuator 7 with the U-shaped head 14 until the marks on the U-shaped head 14 are aligned with the lasers of the CT scanner 1. The arranged automatic robotic apparatus is fixed in place by retainers. The active multilink actuator 7 with the U-shaped head 14 is moved out from the aperture of the CT scanner 1 and stays in the initial position so as not to interfere with the course of the patient scanning.

Figure 3:
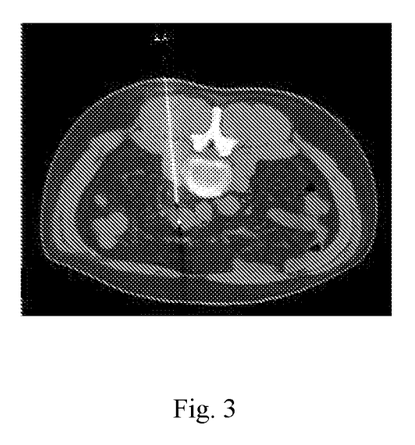
FIG. 3 shows an image of a CT virtual slice depicting automatic planning of the biopsy needle advancement trajectory.

Then the patient is fully undressed, laid onto the CT scanner table 2 and scanned with the aid of the CT scanner 1 in the supposed area of a minimally invasive surgical procedure. An excursion control sensor is turned on for scanning of the patient's mobile organs. Series of virtual CT slices of a focal mass, as produced by the CT scanner computer system, are sent to the robotic apparatus computer system 4 which is used for mapping out the course of and modeling a needle biopsy procedure (with the aid of a special software). The 3D virtual CT slices, as received by the robotic apparatus computer system 4, are subjected to a computerized analysis for the purposes of automatically setting up optimal parameters and conditions for a robotic surgical procedure (with the aid of a special software), namely, the robotic apparatus computer system 4 determines in a 3D projection on said virtual CT slices:
- a point of virtual contact between the hollow U-shaped head 14 and the patient's body (the automatic robotic apparatus performs planning and modeling of an accurate and safe movement of the active multilink actuator 7 to the contact area);
- an area where the hollow U-shaped head contacts the patient;
- points of entry are determined for the guide intratissular anesthesia needle 18 and the biopsy needle 19, and all anesthesia steps required are determined with due regard to individual specific features of each patient;

an optical trajectory for advancing the biopsy needle 19 is determined.

Points of entry for the needles 18 and 19 are determined by finding the air-skin edge according to a HU density. Routes for the intratissular anesthesia needle 18 are determined by a difference between densities of the skin and the muscular tissue layers. Routes for the biopsy needle 19 are determined with due regard to the possibility of minimum action on vessels and critical organs. Routes for the needles 18, 19 are determined with the possibility of correcting the procedure course by the operator. In order to ensure minimum action on vessels and critical organs, a scan with the aid of the CT scanner 1 may be conducted with intravenous contrasting. Moreover, in some cases respiration may be monitored.

In order to monitor respiration, before conducting a biopsy procedure on complex movable areas a sensor for chest excursion (not shown in the Figures) is connected to the automatic robotic apparatus. A strap is attached to the patient, which monitors changes in the chest volume. Also, glasses are put onto the patient's eyes beforehand, which depict a curve of his/her respiration during a scan, and a respiration curve in the real time mode. During a scan the patient should make an inhalation equal to his/her inhalation depth. However, as it is said above, it may be done in extreme cases, during a chest biopsy procedure only, and may not be practiced for patients of advanced age who have difficulties with such a manipulation.

After that, the proposed automatic robotic apparatus starts conducting a minimally invasive surgical procedure with preset optimal conditions and parameters.

During the whole procedure the automatic robotic apparatus is connected to the CT scanner 1 and is capable of exercising full control over the CT scanner 1, in particular for ensuring the possibility of controlling the table 2 and monitoring its angle of inclination, and for ensuring the possibility of conducting a scan.

After the planning procedure is completed, the needle biopsy procedure is started and calculated. The size of the hollow U-shaped head 14 depends on the type of a biopsy needle 19 selected, which length may vary in the range from 10 to 30 cm, the size of the gantry aperture of the CT scanner 1 is 70 cm. Then, the patient on the table 2 of the CT scanner 1 is moved so as to provide a space required for a needle biopsy procedure. In some rare cases, this manipulation may require to move him/her to a side, or to the belly. The robotic arm 6 determines a distance from the patient's surface to the maximum upper point of the aperture 5, using HU data. In a case where such a distance is insufficient for conducting a minimally invasive surgical procedure, the robotic arm 6 issues instructions to move the patient further, until this distance is sufficient for accurate and safe movement of the active multilink actuator 7 of the robotic arm 6. When the active multilink actuator 7 with the hollow U-shaped head 14 is within the aperture 5 of the CT scanner 1, the hollow U-shaped head 14 contacts the skin surface, thus activating the pressure sensor, and the robotic arm 6 stops moving. Then, the CT scanner 1 may change, if necessary, the angle of inclination of the table 2 and, at the same time, the positioning angle of the hollow U-shaped head 14. It is important that, if during the planning procedure the CT scanner 1 was inclined toward the patient's legs while the patient lies with his/her head in the gantry of the CT scanner, the robotic arm 6 change its position correspondingly to maintain the access to the aperture 5. In such a case the movable robotic arm 6 should be positioned correspondingly and the calibration procedure should be repeated.

When all the conditions and parameters are matched between the CT scanner 1 and the robotic arm 6 for a successful and reliable procedure, in particular an angle of inclination of the table 2 and an optimal distance between the robotic arm 6 and the gantry of the CT scanner 1, scanning is conducted, namely, the CT scanner 1 conducts one scan in order the operator may inspect the position of the hollow U-shaped head 14. The course of the procedure is depicted on the control scan. Then, an antiseptic for disinfection of the surface and an anesthetic for surface anesthesia are ejected from the aerosol cylinders 9 and, if necessary, from the piston mechanism 10, said antiseptic and anesthetic are moved via the rubber tubes 11, passed within the active multilink actuator 7, enter, via the connector 13, into the hollow U-shaped head 14, specifically into the through hole 17 intended for ejecting the surface anesthesia drugs onto the fixed area of the patient's skin.

Figure 4:
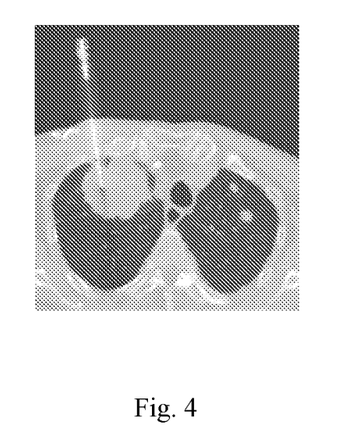
FIG. 4 shows an image of a virtual CT slice depicting biopsy needle advancement in the real-time mode.

Then, the guide needle 18 is advanced for giving intratissular anesthesia and enters under the patient's skin. At this time a control scan is conducted. The operator evaluates the parameters and conditions in the position of the needle 18. Then, the intratissular anesthesia needle 18 is advanced under the skin layer-by layer, introducing the anesthetic in accordance with the preset parameters and conditions. At this time the CT scanner 1 continues making control scans. Upon completion of the anesthesia procedure, the intratissular anesthesia needle 18 is accurately returned to the initial position. Then, the biopsy needle 19 is advanced for conducting a needle biopsy procedure by moving it to the site of interest for collecting a sample. During this, the CT scanner 1 conducts scanning of the manipulation course and displays all the actions on the monitor screen of the robotic apparatus computer system 4. As soon as the biopsy needle 19 reaches the selected point, a sample is collected, and the needle is returned to the initial position.

If selected sites require respiration monitoring, the procedure is conducted in synchronization with respiration according to a respiration curve registered before. The robotic arm 6 conducts the manipulation at the time when the real-time curve coincides with the loaded one, and the patient is moved according to the HU evaluation for the site selected. If the patient has moved, the robotic arm 6 will issue a corresponding signal.

It is important to note in this point that the active multilink actuator 7 has several links for ensuring mobility. The cables, shafts, hollow tubes, which connect the robotic arm 6 to the hollow U-shaped head 14, are carried out by the active multilink actuator 7. The connector 13, which is arranged on the end of the active actuator 7, is made with the possibility of coupling its mechanisms with the hollow U-shaped head 14 in order the latter may perform certain movements (straight, rotational, etc.) and move the needles 18 and 19 and deliver medical preparations (for anesthesia) and make other, preset movements and rotations in accordance with the preset parameters and conditions for conducting a successful and reliable needle biopsy procedure.

For an unforeseen emergency situation, such as a blackout, a strong movement of the patient, an error during the procedure, etc., the robotic arm 6 is equipped with the emergency stop button. It should be pressed for turning off the power supply to the mechanisms involved in the proposed minimally invasive surgical procedure, and in such a case the needles 18 and 19 are returned to their respective initial positions under the action of their respective springs, and the servo drives 16 may rotate freely when the power is shut off.

EXAMPLE 1

A man aged 47.

A neoplasm in the upper lobe of the right lung with a size up to 0.5 cm was identified during a planned X-ray study of the chest organs. The patient was directed to a hospital for further examination.

St. praesens: temperature—36.7, respiratory rate—22 breaths per minute, heart rate—71 beats per minute.

General analysis of urea and blood—no changes.

Complaints: does not make actively.

Bad habits: smoking from the age of 12.

A puncture under the X-ray radiography control is difficult due to a small size of a neoplasm. The patient was subjected to a control CT study, during which a neoplasm of rounded shape with the size of up to 0.5 cm was identified in the upper lobe of the right lung.

No other changes in the chest organs were identified. A decision was taken to conduct a needle biopsy of this site according to the proposed minimally invasive surgical procedure under control of a CT scanner. The data obtained by the CT scanner were transmitted to the control computer system of the automatic robotic apparatus, which was used for modeling and mapping out the course of the needle biopsy procedure, and optimal parameters and conditions for the procedure were determined.

The data was transmitted to the automatic robotic apparatus (the robotic arm 6 with the computer system 4) that conducted the procedure, using the hollow U-shaped head 14 for a needle biopsy. During the manipulation the CT scanner 1 continuously scanned the entire course of the procedure for exercising control over important advancements of the intratissular anesthesia needle 18 and the biopsy needle 19; anesthesia was made also. In this way, reliable data (images) on hitting the focal mass with the needle 19 was obtained, and a sample of a histological material was collected therefrom. The sample was sent to a laboratory for analysis. An epidermoid carcinoma was identified.

Diagnosis: an epidermoid carcinoma in the upper lobe of the right lung.

The proposed method enabled to identify a carcinoma in the lung that was accidentally found during the planned examination. An immediate needle biopsy of small masses is possible only with the use of the proposed automatic robotic system (the robotic arm 6 with the computer system 4), since it is operated in connection with the CT scanner 1, is clearly and reliably oriented according to coordinates and takes the patient's chest excursion into account, which enables to reliably and successfully conduct a needle biopsy of small masses that are inaccessible in an X-ray study.

No damage of critical organs was identified, the patient had minimum painful sensations, and no infection was determined.

EXAMPLE 2

A man aged 57.

Arrived with complaints of the skin icteritiousness, fever, general malaise, weight loss, changed color of feces and urea. The patient was placed in a hospital, a cholelithiasis suspected. A US-procedure identified a small concrement in the gallbladder projection and an enlargement of the intra- hepatic bile ducts. In order to specify the cause of said enlargement of the intrahepatic bile ducts, the patient was subjected to MR cholangiography. A enlargement of the intrahepatic bile ducts with an obstruction in the bifurcation of the common hepatic duct was found, and a neoplasm in this site was suspected.

It was not possible to conduct a biopsy procedure under the US-control for the patient due to a great volume of gas in the intestines, typical stone artifacts in the gallbladder and problems with imaging of the point of narrowing. A CT scan with intravenous contrasting was conducted which identified an accumulation of the contrast preparation in the projection of the common hepatic duct. The data obtained from the CT scanner was transmitted to the computer system 4 used for controlling the automatic robotic system that performed modeling and mapping out the needle biopsy procedure and determined optimal parameters and conditions for the needle biopsy procedure.

The data was transmitted to the automatic robotic apparatus (the robotic arm 6 with the computer system 4) that conducted the procedure, using the hollow U-shaped head 14 for a needle biopsy.

During the manipulation the CT scanner 1 continuously scanned the entire course of the procedure for exercising control over important advancements of the intratissular anesthesia needle 18 and the biopsy needle 19; anesthesia was given as well. In this way reliable data (images) on hitting the focal mass with the needle 19 was obtained, and a sample of a histological material was collected therefrom. The sample was sent to a laboratory for analysis.

Histology: high-differentiated adenocarcinoma.

In the result of the needle biopsy procedure an early-stage mass was identified in a point awkward for a needle biopsy under the US-control.

The needle biopsy procedure was conducted accurately and reliably, no critical organs were damaged, no painful sensations were experienced, no breaks of the skin integrity were made. The patient quickly recovered after this procedure.

EXAMPLE 3

A girl aged 18.

Arrived in a hospital with complaints of weakness, general malaise, temperature rise to 37.5. When evaluating a chest organ X-ray picture, a mediastinal lymphadenopathy was suspected. A CT scan of the chest organs was recommended. A CT scan may identify a mediastinal lymphadenopathy for all groups of the lymph nodes. In order to specify the diagnosis, it was decided to conduct a needle biopsy of the intrathoracic lymph nodes with the use of the proposed method of conducting minimally invasive surgical procedure, because no differentiation of the intrathoracic lymph nodes may be made on a conventional X-ray picture, and the ultrasonic technique is unavailable for a needle biopsy of the mediastinum.

The data obtained from the CT scanner was transmitted to the computer system 4 used for controlling the automatic robotic system that performed modeling and mapping out of a needle biopsy procedure and determined optimal parameters and conditions for that needle biopsy procedure.

The data was transmitted to the automatic robotic apparatus (the robotic arm 6 with the computer system 4) that conducted the procedure, using the hollow U-shaped head 14 for a needle biopsy.

During the manipulation the CT scanner 1 continuously scanned the entire course of the procedure for exercising control over important advancements of the intratissular anesthesia needle 18 and the biopsy needle 19; anesthesia was given as well. In this way reliable data (images) on hitting the focal mass with the needle 19 was obtained, and a sample of a histological material therefrom was collected reliably and successfully. The sample was sent to a laboratory for analysis.

The obtained material was transmitted for a histological study, the conclusion—noncaseified epithelioid granulomas.

Diagnosis: sarcoidosis.

This method of a needle biopsy enables to puncture structures with high accuracy and under continuous control by a doctor, but without his/her direct intervention, which provides the possibility of studying areas with adjoining vitally important organs without the risk of complications.

During the procedure no critical organs were affected, the skin integrity was not violated, no infection development was found.

EXAMPLE 4

A woman aged 45.

An excerpt from the anamnesis: resection of the left kidney due to a renal cell carcinoma. She was subjected to a planned examination on a CT scanner, a neoplasm was found in the left adrenal gland.

The proposed method was selected for a needle biopsy, since it was extremely difficult to image the adrenal glands by an ultrasonic scanning. The sample collected during the biopsy procedure showed a metastasis of a renal cell carcinoma.

The data obtained from the CT scanner was transmitted to the computer system 4 used for controlling the automatic robotic system that performed modeling and mapping out a needle biopsy procedure and determined optimal parameters and conditions for that needle biopsy procedure.

The data was transmitted to the automatic robotic apparatus (the robotic arm 6 with the computer system 4) that conducted the procedure, using the hollow U-shaped head 14 for a needle biopsy.

During the manipulation the CT scanner 1 continuously scanned the entire course of the procedure for exercising control over important advancements of the intratissular anesthesia needle 18 and the biopsy needle 19; anesthesia was given as well. In this way reliable data (images) on hitting the focal mass with the needle 19 was obtained, and a sample of a histological material therefrom was collected reliably and successfully. The sample was sent to a laboratory for analysis.

The proposed method may be used for puncturing masses in hardly accessible sites quickly and operatively, without risks of complications and without any complex preliminary preparation.

No complications and infections were identified in the patient, the skin integrity was not violated.

According to the patient, her general state was good, the recovery was quick.

EXAMPLE 5

A man aged 33.

Arrived with complaints of weakness, poor appetite, weight loss.

An excerpt from the anamnesis: HIV-infected.

No pathology was found on an X-ray picture of the chest organs, An ultrasonic scanning of the abdominal cavity organs and the small pelvis organs showed the normal state.

During a MRI procedure single enlarged lymph nodes partially fused in conglomerates were found in the small pelvis. Due to poor imaging during an ultrasonic scanning, a decision was taken to use the proposed method under the CT scanner control. During mapping out the course of and modeling the procedure itself in the computer system the data obtained from the CT scanner was superposed, which facilitated imaging of masses in the small pelvis and determining access points for the biopsy needle 19 and the guide needle 18 for intratissular anesthesia.

During the manipulation the CT scanner 1 continuously scanned the entire course of the procedure for exercising control over important advancements of the intratissular anesthesia needle 18 and the biopsy needle 19; anesthesia was given as well. In this way reliable data (images) on hitting the focal mass with the needle 19 was obtained, and a sample of a histological material was collected therefrom reliably and successfully. The sample was sent to a laboratory for analysis.

After the conducted study a tissue sample was obtained. Histology: epithelioid cells and Pirogov-Langhans giant cells present specifically against the background of lymphoid and reticular tissue hyperplasia.

Diagnosis: tuberculosis.

This Example shows that the proposed method may be used for conducting complex biopsy procedures without direct involvement of a surgeon, which enables not to tear personnel from medical practice for conducting diagnostic actions, a harmful action of X-radiation as well as possible harmful actions on personnel in connection with this complex manipulation are precluded, and the possibility of infection entering into a site of a direct minimally invasive surgical procedure is significantly reduced.

According to the patient, he did not experience painful sensations during the procedure, his general state was good after the procedure.

EXAMPLE 6

A man aged 53.

Arrived in a hospital for specifying his diagnosis.

An excerpt from the anamnesis: smoking since 18 years of age.

He considered himself ill for three months since the date when he felt weakness, malaise, rise of temperature to 37.5 degrees and cough accompanied with blood excretion appeared.

An X-ray study was immediately conducted during which a mass was identified in the upper lobe of the left lung, having the size up to 8 mm and an irregular structure with radial contours and a cavity in the center. A CT scan was conducted that identified a similar object and enlarged mediastinal lymph nodes on both sides. A decision was taken to conduct a needle biopsy of this mass under X-ray control. A sample sent for a histological study was not informative.

The second needle biopsy under X-ray control was conducted, the histological report stated that the picture corresponded to inflammatory changes in the lung tissue.

The initial diagnosis of tuberculosis was made for the patient.

A control CT scan was scheduled for conducting in 2 weeks. During this period the general state was improved, the temperature was normalized. Other reactions specific for tuberculosis were negative. During the control CT scan small positive dynamics was determined, since the mass dimensions slightly decreased. Due to the absence of a reaction specific for tuberculosis, it was recommended to conduct one more examination of the patient for the purpose of determining the causation of the disease. Due to low information value of the two previous needle biopsy procedures, a decision was taken to subject the patient to a manipulation with the use of the proposed method of minimally invasive surgical procedure.

Before conducting a needle biopsy, the patient's chest was studied with contrasting on the CT scanner 1. The above-said site actively accumulated the contrast preparation along the periphery from the cavity. The data was transmitted from the CT scanner 1 to the robotic apparatus computer system 4 for the purpose of mapping out the course of and modeling a needle biopsy procedure as well as for determining all parameters and conditions optimal for that needle biopsy procedure.

The data was transmitted to the automatic robotic apparatus (the robotic arm 6 with the computer system 4), which conducted the manipulation with the use of the hollow U-shaped biopsy head 14.

During the manipulation the CT scanner 1 continuously scanned the entire course of the procedure for exercising control over important advancements of the intratissular anesthesia needle 18 and the biopsy needle 19; anesthesia was given as well. In this way reliable data (images) on hitting the mass with the needle 19 was obtained, and a sample of a histological material was collected reliably and successfully from the site where the contrasting preparation was accumulated most actively.

The material sample was sent for a histological study.

Opinion: epidermoid carcinoma.

Diagnosis: an epidermoid carcinoma in the upper lobe of the left lung.

This Example shows that the proposed method of minimally invasive surgical procedure provides the possibility of conducting a needle biopsy of not only a mass itself, but also a selected mass site, and obtaining a reliable, most accurate result.

No damage of the patient's critical organs were identified; painful sensations were minimum, no infections were identified, the skin integrity was not violated, the procedure was conducted quickly and insensibly. The post-procedure recovery was quick and easy.

Thus, the proposed method may be most successfully used for conducting a minimally invasive surgical procedure, namely, a needle biopsy of the organs of the chest, the abdominal cavity, the small pelvis and the limbs.

What is claimed is:

1. An automatic robotic apparatus for conducting a minimally invasive surgical procedure, comprising:
   a robotic apparatus computer system;
   a computerized tomography (CT) scanner computer system being in communication with said robotic apparatus computer system so as to receive and process virtual CT slices of a focal mass transmitted by said CT scanner computer system and so as to map out and model the minimally invasive surgical procedure; and
   a robotic arm being in communication with said robotic apparatus computer system,
   wherein said robotic arm comprises:
      a movable member having a distal end portion with a connector and a proximal end portion opposite said distal end portion;
      a control unit being in communication with said robotic apparatus computer system;
      a plurality of servo drives being connected to an active multilink actuator and being in communication with said control unit so as to set a position of said active multilink actuator;
      a pressurized anesthetic cylinder and a pressurized antiseptic cylinder at said proximal end portion,
      a hollow head being attached at said connector of said distal end portion and having a U-shaped longitudinal cross-section, said hollow head having an open base end with an open base width and a base width portion with a base width, said base width portion being adjacent to said open base end, said open base width being greater than said base width, said base width increasing toward said open base end;
      a means for dispensing from said pressurized anesthetic cylinder through said hollow head, the means for dispensing being in communication with said robotic apparatus computer system,
   wherein the means for dispensing is comprised of an anesthetic guide needle in fluid connection with said pressurized anesthetic cylinder; and
      a means for conducting a transcutaneous needle biopsy, the means for conducting being connected to said hollow head and being in communication with said robotic apparatus computer system,
   wherein the means for conducting is comprised of a biopsy guide needle extended from said hollow head so as to perform a needle biopsy; and
      a needle control unit connected to said anesthetic guide needle and said biopsy guide needle, said needle control unit being in communication with said robotic apparatus computer system.

2. The automatic robotic apparatus, according to claim 1, further comprising:
   an antiseptic contained in said pressurized antiseptic cylinder; and
   an anesthetic contained in said pressurized anesthetic cylinder.

3. The automatic robotic apparatus according to claim 1, further comprising a robotic arm case housing at least a portion of said robotic arm so as to fixedly attach said robotic arm to one of a group consisting of: a floor and a ceiling.

4. The automatic robotic apparatus according to claim 1, further comprising a robotic arm case housing at least a portion of said robotic arm, said robotic arm case and being comprised of movable wheels so as to be mobile.

5. The automatic robotic apparatus according to claim 1, wherein said robotic arm is further comprised of an instant stop button in communication with said needle control unit so as to trigger an emergency stop.

6. The automatic robotic apparatus according to claim 1, wherein the means for dispensing is further comprised of a piston mechanism and an electric motor.

7. The automatic robotic apparatus according to claim 6, wherein the means for dispensing is further comprised of a cylindrical container, said piston mechanism being arranged in said cylindrical container.

8. The automatic robotic apparatus according to claim 1, wherein said movable member is comprised of said active multilink actuator.

9. A method of conducting a minimally invasive surgical procedure, comprising the steps of:
   evaluating location and parameters of a focal mass;
   selecting a needle biopsy site determined by an initial computerized tomography (CT) scan; and
   conducting a transcutaneous needle biopsy of a focal mass with an automatic robotic apparatus, according to claim 1, having said biopsy guide needle, wherein the step of conducting comprises the steps of:

producing virtual CT slices by said CT scanner computer system, sending said virtual CT slices to said robotic apparatus computer system, mapping out a course of the needle biopsy with said robotic apparatus computer system, modeling the needle biopsy with said robotic apparatus computer system, subjecting said virtual CT slices to a computerized analysis by said robotic apparatus computer system so as to automatically establish parameters and conditions of conducting a robotic surgical procedure to be performed by the automatic robotic apparatus, contacting said hollow head at said needle biopsy site after the parameters and conditions are established, applying surface and intratissular anesthesia at said needle biopsy site, advancing said biopsy guide needle so as to collect a tissue sample, and scanning said needle biopsy site with a CT scanner connected to said CT scanner computer system so as to monitor said course and the established parameters and conditions.

10. The method of conducting a minimally invasive surgical procedure according to claim 9, wherein the step of subjecting said virtual CT slices to a computerized analysis by said robotic computer system further comprises the steps of:

determining a virtual area of contact for said hollow head, determining entry points and routes of said anesthetic guide needle-14, determining steps of applying surface anesthesia and intratissular anesthesia, and determining a site and routes of said biopsy guide needle, wherein the step of mapping out further comprises the step of:

planning advancement of said movable member relative to said virtual area of contact, and wherein the step of modeling further comprises the step of:

modeling advancement of said movable member relative to said virtual area of contact.

11. The method of conducting a minimally invasive surgical procedure according to claim 10, wherein the step of determining entry points and routes of said anesthetic guide needle comprises a step of: identifying entry points by an air-skin edge under an HU density.

12. The method of conducting a minimally invasive surgical procedure according to claim 10, wherein the step of determining entry points and routes of said anesthetic guide needle comprises a step of: determining routes by a difference between densities of skin and muscular tissue layers.

13. The method of conducting a minimally invasive surgical procedure according to claim 12, further comprising a step of: correcting said routes by manual control.

14. The method of conducting a minimally invasive surgical procedure according to claim 12, wherein the step of determining entry points and routes of said biopsy guide needle comprises a step of: determining routes by exerting a minimum action on vessels and organs.

15. The method of conducting a minimally invasive surgical procedure according to claim 14, further comprising a step of: conducting at least one of a group consisting of: an intravenous contrasting CT scan and a magnetic resonance imaging procedure.

16. The method of conducting a minimally invasive surgical procedure according to claim 9, further comprising a step of:

displaying respiration on medical glasses during said initial CT scan and during the step of scanning said needle biopsy site.

17. The method of conducting a minimally invasive surgical procedure according to claim 16, further comprising a step of: displaying an inhalation depth equal in depth to an inhalation during the step of scanning said needle biopsy site.

18. The method of conducting a minimally invasive surgical procedure according to claim 9, further comprising a step of: calibrating said robotic arm according to CT scanner coordinates before the step of subjecting said virtual CT slices to a computerized analysis by said robotic apparatus computer system so as to automatically establish parameters and conditions.

19. The method of conducting a minimally invasive surgical procedure according to claim 18, wherein the step of calibrating is comprised of the steps of:

moving said hollow head with said movable member so as to match CT scanner lasers set by said CT scanner coordinates; and fixing said robotic arm in place by retainers.

* * * * *